(12) United States Patent
Ascione et al.

(10) Patent No.: US 6,774,175 B2
(45) Date of Patent: Aug. 10, 2004

(54) STABILIZING COMPOSITIONS COMPRISING AT LEAST TWO ANIONIC ASSOCIATIVE POLYMERS, THEIR USE FOR STABILIZATION OF NON-SOLID COMPOSITIONS, AND COMPOSITIONS COMPRISING AT LEAST ONE STABILIZING COMPOSITION

(75) Inventors: Jean-Marc Ascione, New York, NY (US); Michael De George, Toms River, NJ (US)

(73) Assignee: L'Oreal S.A., Paris (FR)

( * ) Notice: Subject to any disclaimer, the term of this patent is extended or adjusted under 35 U.S.C. 154(b) by 148 days.

(21) Appl. No.: 09/809,007

(22) Filed: Mar. 16, 2001

(65) Prior Publication Data

US 2002/0156178 A1 Oct. 24, 2002

Related U.S. Application Data

(60) Provisional application No. 60/268,909, filed on Feb. 16, 2001.

(51) Int. Cl.$^7$ .............................. C08L 3/07; C08L 33/04
(52) U.S. Cl. ..................... 524/523; 424/70.1; 424/70.6; 424/70.7; 424/70.16; 424/78.03
(58) Field of Search ......................... 524/523; 424/70.1, 424/70.6, 70.7, 78.03, 70.16, 401

(56) References Cited

U.S. PATENT DOCUMENTS

| | | |
|---|---|---|
| 4,776,855 A | 10/1988 | Pohl et al. |
| 4,806,345 A | 2/1989 | Bhattacharyya |
| RE33,786 E | 1/1992 | Pohl et al. |
| 5,376,146 A | 12/1994 | Casperson et al. |
| 5,393,305 A | 2/1995 | Cohen et al. |

FOREIGN PATENT DOCUMENTS

| | | |
|---|---|---|
| EP | 0 875 241 A2 | 11/1998 |
| EP | 0 875 241 A3 | 3/1999 |
| WO | WO 00/21494 | 4/2000 |

OTHER PUBLICATIONS

Elton et al., Application of Acrylates/Methacrylates/Beheneth–25 Methacrylate Copolymer (ACULYN 28) as a Thickner and Suspending Agent in Cosmetic Formulations and as a Polymeric Emulsifier, GB, No. 428 pp. 1553–1554, XP 000934522, Dec. 1999.*

Elton et al., *Application of Acrylates/Methacrylates/Beheneth–25 Methacrylate Copolymer (Aculyn 28) as a Thickener and Suspending Agent in Cosmetic Formulations and as a Polymeric Emulsifier*, Research Disclosure, Kenneth Mason Publications, Hampshire, Great Britain, No. 428, pp. 1553–1554, XP–000934522, Dec. 1999.

\* cited by examiner

*Primary Examiner*—Robert D. Harlan
(74) *Attorney, Agent, or Firm*—Finnegan, Henderson, Farabow, Garrett & Dunner, L.L.P.

(57) ABSTRACT

Compositions comprising at least one anionic associative polymer comprising at least one carboxylic acid group and at least one ester derived from a fatty alcohol and a carboxylic acid; and at least one additional anionic associative polymer comprising at least one carboxylic acid group and at least one ester derived from an alkoxylated fatty alcohol and a carboxylic acid, wherein the fatty chain of the alkoxylated fatty alcohol comprises more than 18 carbon atoms, and processes for providing physical stability to at least one non-solid composition comprising the same, and for making up, caring for or treating at least one keratinous material.

72 Claims, No Drawings

STABILIZING COMPOSITIONS COMPRISING AT LEAST TWO ANIONIC ASSOCIATIVE POLYMERS, THEIR USE FOR STABILIZATION OF NON-SOLID COMPOSITIONS, AND COMPOSITIONS COMPRISING AT LEAST ONE STABILIZING COMPOSITION

This application is based upon and claims the benefit of priority of U.S. provisional application No. 60/268,909, filed Feb. 16, 2001, the disclosure of which is incorporated herein by reference.

The present invention relates to compositions comprising (i) at least one anionic associative polymer comprising at least one carboxylic acid group and at least one ester derived from a fatty alcohol and a carboxylic acid; and (ii) at least one additional anionic associative polymer comprising at least one carboxylic acid group and at least one ester derived from an alkoxylated fatty alcohol and a carboxylic acid, wherein the fatty chain of the alkoxylated fatty alcohol comprises more than 18 carbon atoms.

When formulating compositions in general, and in particular compositions comprising at least two components, one faces the challenges of chemical stability of the at least two components and physical stability of the composition as a whole. The physical stability, for example, may be important to ensure that a composition exhibits homogeneity, which may, for example, permit homogeneous activity, such as, where the composition is to be used on keratinous material, conditioning activity, cleansing activity and oxidizing activity and/or even distribution to the keratinous material. An non-homogeneous composition may lead to variation in activity that may result in problems with safety and/or performance, and/or variation in viscosity that may also result in performance issues.

Thus, there is a need for compositions that are physically stable and may be used in conjunction with treatments for keratinous materials. The inventors have found that the use of at least one anionic associative polymer and at least one additional anionic associative polymer in a composition may provide physical stability to the composition.

In one embodiment, therefore, the invention provides a composition comprising (i) at least one anionic associative polymer comprising at least carboxylic acid group and at least one ester derived from a fatty alcohol and a carboxylic acid; and (ii) at least one additional anionic associative polymer comprising at least one carboxylic acid group and at least one ester derived from a carboxylic acid and an alkoxylated fatty alcohol wherein the fatty chain of the alkoxylated fatty alcohol comprises more than 18 carbon atoms. In a further embodiment, the at least one anionic associative polymer and the at least one additional anionic associative polymer are present in a combined amount effective to provide stability to at least one non-solid composition different from the composition comprising the at least one anionic associative polymer and the at least one additional anionic associative polymer. As used herein, "at least one" means one or more and thus includes individual components as well as mixtures/combinations. Accordingly, "at least two" means two or more individual components as well as mixtures/combinations.

The inventive compositions may provide physical stability to at least one non-solid composition. As used herein, "non-solid" refers to compositions that are not in a solid state, such as compositions in a liquid state. A "composition," as used herein, means a combination of at least two components.

According to the present invention, the method for providing physical stability to at least one non-solid composition comprises including in the at least one non-solid composition at least one stabilizing composition comprising (i) at least one anionic associative polymer comprising at least one carboxylic acid group and at least one ester derived from a fatty alcohol and a carboxylic acid; and (ii) at least one additional anionic associative polymer comprising at least one carboxylic acid group and at least one ester derived from an alkoxylated fatty alcohol and a carboxylic acid wherein the fatty chain of the alkoxylated fatty alcohol comprises more than 18 carbon atoms. The at least one anionic associative polymer and the at least one additional anionic associative polymer are present in the at least one stabilizing composition in a combined amount effective to provide stability to the at least one non-solid composition.

Further, the invention provides for a method for making up, caring for or treating at least one keratinous material comprising applying to the at least one keratinous material at least one non-solid composition containing, as a stabilizing composition, the combination of (i) at least one anionic associative polymer comprising at least one carboxylic acid group and at least one ester derived from a fatty alcohol and a carboxylic acid; and (ii) at least one additional anionic associative polymer comprising at least one carboxylic acid group and at least one ester derived from an alkoxylated fatty alcohol and a carboxylic acid, wherein the fatty chain of the alkoxylated fatty alcohol comprises more than 18 carbon atoms. The at least one anionic associative polymer and the at least one additional anionic associative polymer are present in the non-solid composition in a combined amount effective to provide stability to the at least one non-solid composition. The at least one keratinous material may be human keratinous material, such as hair, eyelashes, eyebrows, nails, and skin (including lips, facial skin and body).

Another subject of the present invention is a non-solid composition comprising at least one stabilizing composition which comprises (i) at least one anionic associative polymer comprising at least one carboxylic acid group and at least one ester derived from a fatty alcohol and a carboxylic acid; and, (ii) at least one additional anionic associative polymer comprising at least one carboxylic acid group and at least one ester derived from an alkoxylated fatty alcohol and a carboxylic acid, wherein the fatty chain of said alkoxylated fatty alcohol comprises more than 18 carbon atoms. The at least one anionic associative polymer and the at least one additional anionic associative polymer are present in the at least one stabilizing composition in a combined amount effective to provide stability to the at least one non-solid composition.

The non-solid compositions of the invention may be, for example, suitable for application to at least one keratinous material. The inventive non-solid compositions may be useful for making up, for care of and/or for treatment of at least one keratinous material. Non-limiting examples of such non-solid compositions include non-solid compositions for making up keratinous fibers, such as mascara compositions, and compositions for eyebrows; non-solid compositions for making up the skin of the face and/or body, such as lip compositions, eyeliner compositions, eyeshadow compositions, blusher compositions, foundation compositions, and concealer compositions; non-solid compositions for making up, caring for and/or treating the nails, such as nail polish compositions; non-solid compositions for care of and/or treatment of the skin of the face and/or body, such as moisturizing compositions, and compositions comprising medicaments which may be applied topically; non-solid compositions for making up the hair, such as topical hair coloring compositions (e.g., hair mascara) and hair styling compositions (such as gels, mousses, sprays, lacquers, pomades, and glossers); and non-solid compositions for caring for and/or treating hair, such as shampoo compositions, conditioning compositions, hair dyeing compositions, hair bleaching compositions, hair relaxing compositions, and permanent hair waving compositions.

In one embodiment, the non-solid compositions of the invention are physically stable. As used herein, "physical stability" is tested by placing the composition in a controlled environment chamber for 8 weeks at 45° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for phase separation. A composition is considered to lack physical stability if separation of the phases of a composition is observed by the human eye. Accordingly, a composition is considered "physically stable" if no phase separation is observed at 8 weeks in the above test. As used herein, therefore, "stabilization" means making a composition "physically stable" as just defined.

The at least one anionic associative polymer of the present invention comprises at least one carboxylic acid group and at least one ester derived from a fatty alcohol and a carboxylic acid. The fatty alcohol, for example, may be chosen from $C_8$ to $C_{36}$ fatty alcohols.

In a further embodiment, the at least one anionic associative polymer may be chosen from copolymers derived from (i) at least one monomer chosen from $C_{10}$–$C_{30}$ alkyl acrylates and (ii) at least one monomer comprising at least one carboxylic acid group. The at least one anionic associative polymer may further comprise at least one unit comprising at least one ester chosen from esters derived from acrylic acid and esters derived from methacrylic acid. The at least one monomer comprising at least one carboxylic acid group, in one embodiment, may be chosen from acrylic acid and methacrylic acid. In a further embodiment, the at least one anionic associative polymer may be crosslinked with at least one allyl ether chosen from allyl ethers of sucrose and allyl ethers of pentaerythritol.

Non-limiting examples of the at least one anionic associative polymer which may be used in the composition according to the present invention include Acrylates/C10–30 Alkyl Acrylate Crosspolymers, which are sold by Goodrich under the names Carbopol 1342, Carbopol 1382, Carbopol ETD 2020, Pemulen TR1, and Pemulen TR-2.

The at least one additional anionic associative polymer of the present invention comprises at least one carboxylic acid group and at least one ester derived from an alkoxylated fatty alcohol and a carboxylic acid, wherein the fatty chain of the alkoxylated fatty alcohol comprises more than 18 carbon atoms. The alkoxylated fatty alcohol, for example, may be chosen from polyethylene glycol ethers wherein the fatty chain of the alkoxylated fatty alcohol comprises more than 18 carbon atoms.

In one embodiment, the at least one additional anionic associative polymer may be chosen from copolymers derived from (i) at least one monomer comprising at least one ester derived from a carboxylic acid and a polyethylene glycol ether wherein the polyethylene glycol ether comprises at least one fatty chain comprising more than 18 carbon atoms, and (ii) at least one monomer comprising at least one carboxylic acid group. The at least one monomer comprising at least one carboxylic acid group, in one embodiment, may be chosen from acrylic acid and methacrylic acid. The at least one additional anionic associative polymer may further comprise at least one unit comprising at least one ester chosen from esters derived from acrylic acid and a polyethylene glycol ether comprising at least one fatty chain comprising more than 18 carbon atoms, and esters derived from methacrylic acid and a polyethylene glycol ether comprising at least one fatty chain comprising more than 18 carbon atoms. The polyethylene glycol ether, for example, may be chosen from polyethylene glycol ethers of at least one alcohol chosen from nonadecanol, arachidyl alcohol, heneicosanol, behenyl alcohol, tricosanol, triacontanol, and hentriacontanol.

A non-limiting example of the at least one additional anionic associative polymer which may be used in the composition according to the present invention is Acrylates/Beheneth-25 Methacrylate Copolymer, which is sold by Rohm & Haas under the name Aculyn 28.

As described above, in one embodiment, the at least one anionic associative polymer and the at least one additional anionic associative polymer are present in a combined amount effective to provide stability to at least one non-solid composition. While the presence of only one of the anionic associative polymers may be sufficient to physically stabilize the non-solid composition, this result often requires too high a concentration of a single anionic associative polymer, and, thus, the resulting composition is too viscous for the application envisaged. Furthermore, a very viscous composition may only slow down phase separation as opposed to stabilizing the composition. However, the use of both the at least one anionic associative polymer and the at least one additional associative polymer of the present invention, may result in a physically stable composition at a lower total concentration of anionic associative polymers as compared to the concentration of a single anionic associative polymer that would be required to result in a physically stable composition.

One of skill in the art, armed with the physical stability test described herein, may choose the concentration of the at least one anionic associative polymer and the concentration of at least one additional anionic associative polymer based on the physical stability desired and the application envisaged. Further, the skilled artisan may also use the physical stability test to choose the combination of associative polymers which results in the desired stability for the application.

For example, in one embodiment, in a composition for chemical treatment of hair, the at least one anionic associative polymer may be present in an amount generally ranging from 0.01% to 2.50% by weight relative to the total weight of the composition, and the at least one additional anionic associative polymer may be present in the composition in an amount generally ranging from 0.01% to 5.00% by weight relative to the total weight of the composition. One of skill in the art would recognize that the envisioned applications of the inventive compositions are very diverse, and thus, the above ranges of concentrations are merely suggestive for one particular application.

The composition of the present invention may also comprise at least one adjuvants conventionally used in compositions for at least one keratinous material, such as, but not limited to, anionic surfactants, cationic surfactants, nonionic surfactants, and amphoteric surfactants; anionic polymers other than the anionic polymers discussed above, cationic polymers, nonionic polymers, and amphoteric polymers; inorganic thickeners and organic thickeners; conditioners; chelating agents, antioxidants; stabilizing agents; propellants; sequestering agents; emollients; humectants;

fragrances; acidifying and basifying agents; chelating agents, moisturizing agents; vitamins; essential fatty acids; proteins and protein derivatives; preservatives; and opacifiers.

Needless to say, a person skilled in the art will take care to select the optional adjuvant(s) such that the advantageous properties intrinsically associated with the invention are not, or are not substantially, adversely affected by the addition(s) envisaged. Again, one of skill in the art will be guided by the physical stability test described herein.

As previously described, the at least one anionic associative polymer and at least one additional anionic associative polymer may be useful for stabilizing any non-solid compositions. For example, these anionic associative polymers can be used in non-solid compositions suitable for application to keratinous materials.

According to the present invention, the inventive non-solid compositions may be in a form, for example, chosen from an aqueous emulsion, a suspension, a dispersion, a gel, a spray, an aerosol foam, a cream, a lotion, a solution, a paste, and a hydroalcoholic lotion.

The invention also provides a method for providing physical stability to at least one non-solid composition comprising including in the at least one non-solid composition at least one stabilizing composition comprising (i) at least one anionic associative polymer comprising at least one carboxylic acid group and at least one ester derived from a fatty alcohol and a carboxylic acid; (ii) and at least one additional anionic associative polymer comprising at least one carboxylic acid group and at least one ester derived from an alkoxylated fatty alcohol and a carboxylic acid. The fatty chain of the alkoxylated fatty alcohol comprises more than 18 carbon atoms. The at least one anionic associative polymer and the at least one additional anionic associative polymer are present in a combined amount effective to provide physical stability to the at least one non-solid composition.

Another subject of the present invention is a multi-compartment kit for making up, treating or caring for at least one keratinous material, wherein the kit has at least two separate compartments. The first compartment contains a composition comprising at least one stabilizing composition comprising (i) at least one anionic associative polymer comprising at least one carboxylic acid group and at least one ester of a fatty alcohol and a carboxylic acid; and (ii) at least one additional anionic associative polymer comprising at least one carboxylic acid group and at least one ester derived from an alkoxylated fatty alcohol and a carboxylic acid, wherein the fatty chain of the alkoxylated fatty alcohol comprises more than 18 carbon atoms. The second compartment contains a composition for making up, treating or care of the at least of one keratinous material, e.g., dyeing, bleaching, permanent waving, relaxing, conditioning, shampoo or styling.

Yet another subject of the present invention is a method for making up, caring for or treating at least one keratinous material comprising applying to the at least one keratinous material at least one non-solid composition comprising at least one stabilizing composition comprising (i) at least one anionic associative-polymer comprising at least one carboxylic acid group and at least one ester derived from a fatty alcohol and a carboxylic acid; and (ii) at least one additional anionic associative polymer comprising at least one carboxylic acid group and at least one ester derived from an alkoxylated fatty alcohol and a carboxylic acid. The fatty chain of the alkoxylated fatty alcohol comprises more than 18 carbon atoms, wherein the at least one anionic associative polymer and the at least one additional anionic associative polymer are present in a combined amount effective to provide stability to the at least one non-solid composition. The at least one keratinous material may be chosen from human keratinous materials, such as hair, facial skin, lips, skin on the body, eyelashes, eyebrows, and nails.

The example given below, purely by way of illustration and with no limiting nature, will allow the invention to be understood more clearly.

EXAMPLE

Stabilization of a Non-solid Composition Using a Combination of Anionic Associative Polymers The four following compositions, $A_1$, $A_2$, $A_3$ and $A_4$ were prepared. Comparative Composition $A_1$ contained the anionic associative polymer, Acrylates/C10–30 Alkyl Acrylate Crosspolymer (Carbopol ETD 2020), but did not contain the additional anionic associative polymer as described herein. Comparative Composition $A_2$ contained the additional anionic associative polymer, Acrylates/Beheneth-25 Methacrylate Copolymer (Aculyn,28), but did not contain the anionic associative polymer as described herein. Inventive Composition $A_3$ contained the anionic associative polymer, Acrylates/C10–30 Alkyl Acrylate Crosspolymer (Carbopol ETD 2020) and the additional anionic associative polymer, Acrylates/Beheneth-25 Methacrylate Copolymer (Aculyn 28). Comparative Composition $A_4$, contained the anionic associative polymer, Acrylates/C10–30 Alkyl Acrylate Crosspolymer (Carbopol ETD 2020) and an additional anionic associative polymer, Acrylates/Steareth-20 Methacrylate Copolymer (Aculyn 22), different from the at least one additional associative polymer according to the present invention.

| | CONCENTRATION OF COMPONENT (Percent) | | | |
|---|---|---|---|---|
| COMPONENT (CTFA Name) | Composition $A_1$ (Comparative) | Composition $A_2$ (Comparative) | Composition $A_3$ (Inventive) | Composition $A_4$ (Comparative) |
| CETETH-10 | 2.25 | 2.25 | 2.25 | 2.25 |
| ISOCETETH-20 | 1.800 | 1.800 | 1.800 | 1.800 |
| CETETH-2 | 1.125 | 1.125 | 1.125 | 1.125 |
| ACRYLATES/ C10–30 ALKYL ACRYLATE CROSSPOLYMER | 0.6 | — | 0.6 | 0.6 |
| ACRYLATES/ BEHENETH-25 METHACRYLATE COPOLYMER | — | 0.3000 | 0.3000 | — |
| ACRYLATES/ STEARETH-20 METHACRYLATE COPOLYMER | — | — | — | 0.3000 |
| PENTASODIUM PENTETATE | 0.0380 | 0.0380 | 0.0380 | 0.0380 |
| PHOSPHORIC ACID | Q.S. pH to 3.5 | Q.S. pH to 3.5 | Q.S. pH to 3.5 | Q.S. pH to 3.5 |
| WATER | Q.S. to 100 | Q.S. to 100 | Q.S. to 100 | Q.S. to 100 |

Results

The visual physical stability of the four compositions, $A_1$, $A_2$, $A_3$, and $A_4$, was observed at 45° C. The results are listed below.

| Compositions | Appearance (45° C.) |
| --- | --- |
| A₁ (comparative) | substantial phase separation (10 days) |
| A₂ (comparative) | substantial phase separation (24 hrs) |
| A₃ (inventive) | no substantial phase separation (8 weeks) |
| A₄ (comparative) | substantial phase separation (24 hrs) |

The results demonstrate that acceptable physical stability was only observed for the composition comprising both at least one anionic associative polymer and at least one additional anionic associative polymer according to the present invention.

What is claimed is:

1. A composition comprising:
   (i) at least one anionic associative polymer comprising at least one carboxylic acid group and at least one ester derived from a fatty alcohol and a carboxylic acid; and
   (ii) at least one additional anionic associative polymer comprising at least one carboxylic acid group and at least one ester derived from an alkoxylated fatty alcohol and a carboxylic acid, wherein the fatty chain of said alkoxylated fatty alcohol comprises more than 18 carbon atoms.

2. The composition according to claim 1, wherein said at least one anionic associative polymer and said at least one additional anionic associative polymer are present in a combined amount effective to provide stability to at least one non-solid composition different from said composition of claim 1.

3. The composition according to claim 1, wherein said fatty alcohol of said at least one anionic associative polymer is chosen from $C_8$ to $C_{36}$ fatty alcohols.

4. The composition according to claim 1, wherein said at least one anionic associative polymer is chosen from copolymers derived from (i) at least one monomer chosen from $C_{10}$–$C_{30}$ alkyl acrylates, and (ii) at least one monomer comprising at least one carboxylic acid group.

5. The composition according to claim 4, wherein said at least one monomer comprising at least one carboxylic acid group is chosen from acrylic acid and methacrylic acid.

6. The composition according to claim 4, wherein said at least one anionic associative polymer further comprises at least one unit comprising at least one ester chosen from esters derived from acrylic acid and esters derived from methacrylic acid.

7. The composition according to claim 6, wherein said at least one anionic associative polymer is crosslinked with at least one allyl ether chosen from allyl ethers of sucrose and allyl ethers of pentaerythritol.

8. The composition according to claim 1, wherein said at least one anionic associative polymer is chosen from Acrylates/C10–30 Alkyl Acrylate Crosspolymers.

9. The composition according to claim 1, wherein said alkoxylated fatty alcohol is chosen from polyethylene glycol ethers.

10. The composition according to claim 1, wherein said at least one additional anionic associative polymer is chosen from copolymers derived from (i) at least one monomer comprising at least one ester derived from a carboxylic acid and a polyethylene glycol ether and (ii) at least one monomer comprising at least one carboxylic acid group.

11. The composition according to claim 10, wherein said at least one monomer comprising at least one carboxylic acid group is chosen from acrylic acid and methacrylic acid.

12. The composition according to claim 10, wherein said at least one additional anionic associative polymer further comprises at least one unit comprising at least one ester chosen from esters derived from acrylic acid and a polyethylene glycol ether, and esters derived from methacrylic acid and a polyethylene glycol ether.

13. The composition according to claim 10, wherein said polyethylene glycol ether is chosen from polyethylene glycol ethers of at least one alcohol chosen from nondecanol, arachidyl alcohol, heneicosanol, behenyl alcohol, tricosanol, triacontanol, and hentriacontanol.

14. The composition according to claim 1, wherein said at least one additional anionic associative polymer is chosen from Acrylates/Beheneth-25 Methacrylate Copolymers.

15. The composition according to claim 1, wherein said at least anionic associative polymer is present in the composition in an amount ranging from 0.01% to 2.5% by weight relative to the total weight of the composition.

16. The composition according to claim 1, wherein said at least one additional anionic associative polymer is present in the composition in an amount ranging from 0.01% to 5.00% by weight relative to the total weight of the composition.

17. The composition according to claim 1, further comprising at least one adjuvant chosen from anionic surfactants, cationic surfactants, nonionic surfactants, amphoteric surfactants, anionic polymers different from said at least one anionic associative polymer and different from said at least one additional anionic associative polymer, nonionic polymers, cationic polymers, amphoteric polymers, inorganic thickeners, organic thickeners, antioxidants, stabilizing agents, oxidizing agents, propellants, sequestering agents, emollients, humectants, fragrances, acidifying agents, basifying agents, chelating agents, moisturizing agents, vitamins, essential fatty acids, proteins, protein derivatives, preservatives, and opacifiers.

18. The composition according to claim 1, wherein said composition is in the form of an aqueous emulsion, a suspension, a dispersion, an aerosol foam, a cream, a lotion, a solution, a paste, a gel, a spray, or a hydroalcoholic lotion.

19. A method for providing physical stability to at least one non-solid composition comprising:
   including in said at least one non-solid composition, at least one stabilizing composition comprising:
   (i) at least one anionic associative polymer comprising at least one carboxylic acid group and at least one ester derived from a fatty alcohol and a carboxylic acid; and
   (ii) at least one additional anionic associative polymer comprising at least one carboxylic acid group and at least one ester derived from an alkoxylated fatty alcohol and a carboxylic acid, wherein the fatty chain of said alkoxylated fatty alcohol comprises more than 18 carbon atoms;
   wherein said at least one anionic associative polymer and said at least one additional anionic associative polymer are present in a combined amount effective to provide stability to said at least one non-solid composition.

20. The method according to claim 19, wherein said fatty alcohol of said at least one anionic associative polymer is chosen from $C_8$ to $C_{36}$ fatty alcohols.

21. The method according to claim 19, wherein said at least one anionic associative polymer is chosen from copolymers derived from (i) at least one monomer chosen from $C_{10}$–$C_{30}$ alkyl acrylates, and (ii) at least one monomer comprising at least one carboxylic acid group.

22. The method according to claim 21, wherein said at least one monomer comprising at least one carboxylic acid group is chosen from acrylic acid and methacrylic acid.

23. The method according to claim 21, wherein said at least one anionic associative polymer further comprises at least one unit comprising at least one ester chosen from esters derived from acrylic acid and esters derived from methacrylic acid.

24. The method according to claim 23, wherein said at least one anionic associative polymer is crosslinked with at least one allyl ether chosen from allyl ethers of sucrose and allyl ethers of pentaerythritol.

25. The method according to claim 19, wherein said at least one anionic associative polymer is chosen from Acrylates/C10–30 Alkyl Acrylate Crosspolymers.

26. The method according to claim 19, wherein said alkoxylated fatty alcohol is chosen from polyethylene glycol ethers.

27. The method according to claim 19, wherein said at least one additional anionic associative polymer is chosen from copolymers derived from (i) at least one monomer comprising at least one ester derived from a carboxylic acid and a polyethylene glycol ether and (ii) at least one monomer comprising at least one carboxylic acid group.

28. The method according to claim 27, wherein said at least one monomer comprising at least one carboxylic acid group is chosen from acrylic acid and methacrylic acid.

29. The method according to claim 27, wherein said at least one additional anionic associative polymer further comprises at least one unit comprising at least one ester chosen from esters derived from acrylic acid and a polyethylene glycol ether, and esters derived from methacrylic acid and a polyethylene glycol ether.

30. The method according to claim 27, wherein said polyethylene glycol ether is chosen from polyethylene glycol ethers of at least one alcohol chosen from nondecanol, arachidyl alcohol, heneicosanol, behenyl alcohol, tricosanol, triacontanol, and hentriacontanol.

31. The method according to claim 27, wherein said at least one additional anionic associative polymer is chosen from Acrylates/Beheneth-25 Methacrylate Copolymers.

32. The method according to claim 19, wherein said at least anionic associative polymer is present in the composition in an amount ranging from 0.01% to 2.5% by weight relative to the total weight of the at least one non-solid composition.

33. The method according to claim 19, wherein said at least one additional anionic associative polymer is present in the composition in an amount ranging from 0.01% to 5.00% by weight relative to the total weight of the at least one non-solid composition.

34. The method according to claim 19, wherein said at least one non-solid composition further comprises at least one adjuvant chosen from anionic surfactants, cationic surfactants, nonionic surfactants, amphoteric surfactants, anionic polymers different from said at least one anionic associative polymer and different from said at least one additional anionic associative polymer, nonionic polymers, cationic polymers, amphoteric polymers, inorganic thickeners, organic thickeners, antioxidants, stabilizing agents, oxidizing agents, propellants, sequestering agents, emollients, humectants, fragrances, acidifying agents, basifying agents, chelating agents, moisturizing agents, vitamins, essential fatty acids, proteins, protein derivatives, preservatives, and opacifiers.

35. The method according to claim 19, wherein said at least one non-solid composition is in the form of an aqueous emulsion, a suspension, a dispersion, an aerosol foam, a cream, a lotion, a solution, a paste, a gel, a spray, or a hydroalcoholic lotion.

36. A method for making up, caring for or treating at least one keratinous material comprising:
 applying to said at least one keratinous material at least one non-solid composition comprising at least one stabilizing composition comprising:
  (i) at least one anionic associative polymer comprising at least one carboxylic acid group and at least one ester derived from a fatty alcohol and a carboxylic acid; and
  (ii) at least one additional anionic associative polymer comprising at least one carboxylic acid group and at least one ester derived from an alkoxylated fatty alcohol and a carboxylic acid, wherein the fatty chain of said alkoxylated fatty alcohol comprises more than 18 carbon atoms;
 wherein said at least one anionic associative polymer and said at least one additional anionic associative polymer are present in a combined amount effective to provide stability to said at least one non-solid composition.

37. A method according to claim 36, wherein said at least one keratinous material is a human keratinous material.

38. A method according to claim 37, wherein said human keratinous material is chosen from hair, facial skin, lips, skin on the body, eyelashes, eyebrows, and nails.

39. The method according to claim 36, wherein said fatty alcohol of said at least one anionic associative polymer is chosen from $C_8$ to $C_{36}$ fatty alcohols.

40. The method according to claim 36, wherein said at least one anionic associative polymer is chosen from copolymers derived from (i) at least one monomer chosen from $C_{10}$–$C_{30}$ alkyl acrylates, and (ii) at least one monomer comprising at least one carboxylic acid group.

41. The method according to claim 40, wherein said at least one monomer comprising at least one carboxylic acid group is chosen from acrylic acid and methacrylic acid.

42. The method according to claim 40, wherein said at least one anionic associative polymer further comprises at least one unit comprising at least one ester chosen from esters derived from acrylic acid and esters derived from methacrylic acid.

43. The method according to claim 42, wherein said at least one anionic associative polymer is crosslinked with at least one allyl ether chosen from allyl ethers of sucrose and allyl ethers of pentaerythritol.

44. The method according to claim 36, wherein said at least one anionic associative polymer is chosen from Acrylates/C10–30 Alkyl Acrylate Crosspolymers.

45. The method according to claim 36, wherein said alkoxylated fatty alcohol is chosen from polyethylene glycol ethers.

46. The method according to claim 36, wherein said at least one additional anionic associative polymer is chosen from copolymers derived from (i) at least one monomer comprising at least one ester derived from a carboxylic acid and a polyethylene glycol ether and (ii) at least one monomer comprising at least one carboxylic acid group.

47. The method according to claim 46, wherein said at least one monomer comprising at least one carboxylic acid group is chosen from acrylic acid and methacrylic acid.

48. The method according to claim 46, wherein said at least one additional anionic associative polymer further comprises at least one unit comprising at least one ester chosen from esters derived from acrylic acid and a polyethylene glycol ether, and esters derived from methacrylic acid and a polyethylene glycol ether.

49. The method according to claim 46, wherein said polyethylene glycol ether is chosen from polyethylene glycol ethers of at least one alcohol chosen from nondecanol, arachidyl alcohol, heneicosanol, behenyl alcohol, tricosanol, triacontanol, and hentriacontanol.

50. The method according to claim 36, wherein said at least one additional anionic associative polymer is chosen from Acrylates/Beheneth-25 Methacrylate Copolymers.

51. The method according to claim 36, wherein said at least anionic associative polymer is present in the composition in an amount ranging from 0.01% to 2.5% by weight relative to the total weight of the at least one non-solid composition.

52. The method according to claim 36, wherein said at least one additional anionic associative polymer is present in the composition in an amount ranging from 0.01% to 5.00% by weight relative to the total weight of the at least one non-solid composition.

53. The method according to claim 36, wherein the at least one non-solid composition further comprises at least one adjuvant chosen from anionic surfactants, cationic surfactants, nonionic surfactants, amphoteric surfactants, anionic polymers different from said at least one anionic associative polymer and different from said at least one additional anionic associative polymer, nonionic polymers, cationic polymers, amphoteric polymers, inorganic thickeners, organic thickeners, antioxidants, stabilizing agents, oxidizing agents, propellants, sequestering agents, emollients, humectants, fragrances, acidifying agents, basifying agents, chelating agents, moisturizing agents, vitamins, essential fatty acids, proteins, protein derivatives, preservatives, and opacifiers.

54. The method according to claim 36, wherein said at least one non-solid composition is in the form of an aqueous emulsion, a suspension, a dispersion, an aerosol foam, a cream, a lotion, a solution, a paste, a gel, a spray, or a hydroalcoholic lotion.

55. A non-solid composition comprising at least one stabilizing composition comprising:
   (i) at least one anionic associative polymer comprising at least one carboxylic acid group and at least one ester derived from a fatty alcohol and a carboxylic acid; and
   (ii) at least one additional anionic associative polymer comprising at least one carboxylic acid group and at least one ester derived from an alkoxylated fatty alcohol and a carboxylic acid, wherein the fatty chain of said alkoxylated fatty alcohol comprises more than 18 carbon atoms,
wherein said at least one anionic associative polymer and said at least one additional anionic associative polymer are present in a combined amount effective to provide stability to said at least one non-solid composition.

56. The composition according to claim 55, wherein said fatty alcohol of said at least one anionic associative polymer is chosen from $C_8$ to $C_{36}$ fatty alcohols.

57. The composition according to claim 55, wherein said at least one anionic associative polymer is chosen from copolymers derived from (i) at least one monomer chosen from $C_{10}$–$C_{30}$ alkyl acrylates, and (ii) at least one monomer comprising at least one carboxylic acid group.

58. The composition according to claim 57, wherein said at least one monomer comprising at least one carboxylic acid group is chosen from acrylic acid and methacrylic acid.

59. The composition according to claim 57, wherein said at least one anionic associative polymer further comprises at least one unit comprising at least one ester chosen from esters derived from acrylic acid and esters derived from methacrylic acid.

60. The composition according to claim 59, wherein said at least one anionic associative polymer is crosslinked with at least one allyl ether chosen from allyl ethers of sucrose and allyl ethers of pentaerythritol.

61. The composition according to claim 55, wherein said at least one anionic associative polymer is chosen from Acrylates/C10–30 Alkyl Acrylate Crosspolymers.

62. The composition according to claim 55, wherein said alkoxylated fatty alcohol is chosen from polyethylene glycol ethers.

63. The composition according to claim 55, wherein said at least one additional anionic associative polymer is chosen from copolymers derived from. (i) at least one monomer comprising at least one ester derived from a carboxylic acid and a polyethylene glycol ether and (ii) at least one monomer comprising at least one carboxylic acid group.

64. The composition according to claim 63, wherein said at least one monomer comprising at least one carboxylic acid group is chosen from acrylic acid and methacrylic acid.

65. The composition according to claim 63, wherein said at, least one additional anionic associative polymer further comprises at least one unit comprising at least one ester chosen from esters derived from acrylic acid and a polyethylene glycol ether, and esters derived from methacrylic acid and a polyethylene glycol ether.

66. The composition according to claim 63, wherein said polyethylene glycol ether is chosen from polyethylene glycol ethers of at least one alcohol chosen from nondecanol, arachidyl alcohol, heneicosanol, behenyl alcohol, tricosanol, triacontanol, and hentriacontanol.

67. The composition according to claim 55, wherein said at least one additional anionic associative polymer is chosen from Acrylates/Beheneth-25 Methacrylate Copolymers.

68. The composition according to claim 55, wherein said at least anionic associative polymer is present in the composition in an amount ranging from 0.01% to 2.5% by weight relative to the total weight of the composition.

69. The composition according to claim 55, wherein said at least one additional anionic associative polymer is present in the composition in an amount ranging from 0.01% to 5.00% by weight relative to the total weight of the composition.

70. The composition according to claim 55, further comprising at least one adjuvant chosen from anionic surfactants, cationic surfactants, nonionic surfactants, amphoteric surfactants, anionic polymers different from said at least one anionic associative polymer and different from said at least one additional anionic associative polymer, nonionic polymers, cationic polymers, amphoteric polymers, inorganic thickeners, organic thickeners, antioxidants, stabilizing agents, oxidizing agents, propellants, sequestering agents, emollients, humectants, fragrances, acidifying agents, basifying agents, chelating agents, moisturizing agents, vitamins, essential fatty acids, proteins, protein derivatives, preservatives, and opacifiers.

71. The composition according to claim 55, wherein said at least one non-solid composition is in the form of an aqueous emulsion, a suspension, a dispersion, an aerosol foam, a cream, a lotion, a solution, a paste, a gel, a spray, or a hydroalcoholic lotion.

72. The composition according to claim 55, wherein said at least one non-solid composition is in the form of a mascara, a composition for eyebrows, a lip composition, an eyeliner, an eyeshadow, a blusher, a foundation, a concealer, a nail composition, a moisturizer, a make up composition for hair, a hair styling composition, a shampoo, a conditioner, a hair dye, a hair bleaching composition, a hair relaxing composition, or a composition for permanent waving hair.

* * * * *

UNITED STATES PATENT AND TRADEMARK OFFICE
CERTIFICATE OF CORRECTION

PATENT NO.    : 6,774,175 B2
DATED         : August 10, 2004
INVENTOR(S)   : Jean-Marc Ascione et al.

It is certified that error appears in the above-identified patent and that said Letters Patent is hereby corrected as shown below:

<u>Column 12,</u>
Line 11, delete period after "from".
Line 18, delete comma after "at".

Signed and Sealed this

First Day of February, 2005

JON W. DUDAS
*Director of the United States Patent and Trademark Office*